United States Patent [19]
Urban

[11] Patent Number: 5,977,355
[45] Date of Patent: Nov. 2, 1999

[54] PROCESSES AND INTERMEDIATES FOR PREPARING 3-AMINO-BENZO(B) AZEPINONES

[75] Inventor: Frank J. Urban, Waterford, Conn.

[73] Assignee: Pfizer Inc., New York, N.Y.

[21] Appl. No.: 08/817,857

[22] PCT Filed: Sep. 13, 1995

[86] PCT No.: PCT/IB95/00754

§ 371 Date: Apr. 17, 1997

§ 102(e) Date: Apr. 17, 1997

[87] PCT Pub. No.: WO96/10564

PCT Pub. Date: Apr. 11, 1996

[51] Int. Cl.[6] .................................................. C07D 223/16
[52] U.S. Cl. ............................................................ 540/523
[58] Field of Search ............................................... 540/523

[56] References Cited

U.S. PATENT DOCUMENTS 5,696,111  12/1997  Baldwin et al. ...................... 514/213

FOREIGN PATENT DOCUMENTS

WO 93/15059  8/1993  WIPO .
WO 94/07483  4/1994  WIPO .

OTHER PUBLICATIONS

Schoen et al. (J. Med. Chem. 1994, 37, 897–906.

Methoden Der Organischen Chemie, 1955, pp. 513–519.

*Primary Examiner*—Mukund J. Shah
*Assistant Examiner*—Bruck Kifle
*Attorney, Agent, or Firm*—Peter C. Richardson; Paul H. Ginsburg; Mark Dryer

[57] ABSTRACT

A process for the preparation of CCK antagonists of the formula

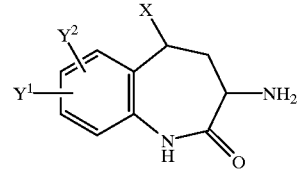

wherein X, $Y^1$ and $Y^2$ are defined above and to novel intermediates used in the process.

4 Claims, No Drawings

PROCESSES AND INTERMEDIATES FOR PREPARING 3-AMINO-BENZO(B) AZEPINONES

The present invention relates to novel processes for the preparation of benzo[b]azepine-2-one CCK antagonists of formula VII, described below, and to novel intermediates used in the processes.

PCT Patent Publication WO 93/15059, published Aug. 5, 1993, refers to the CCK receptor antagonists of formula VII and processes for their preparation.

PCT Patent Publication WO 94/07483, published Apr. 14, 1994, refers to benzo-fused lactam derivatives that are stated to be growth hormone release agents and are prepared in a process analogous to that described in PCT Patent Publication WO 93/15059.

PCT Patent Publication WO 94/07483, published Apr. 14, 1994, generically refers to benzo[b]azepine-2-ones, but does not refer to any specific stereoisomers of these intermediates.

SUMMARY OF THE INVENTION

The present invention relates to the intermediate (+)-cis-(3R)-amino-8-methyl-(5R)-phenyl-1,3,4,5-tetrahydro-benzo[b]azepine-2-one.

The present invention also relates to a process for preparing the diasteriomeric salt (+)-cis-(3R)-amino-8-methyl-(5R)-phenyl-1,3,4,5-tetrahydro-benzo[b]azepine-2-one•(D)-(+)-dibenzoyltartarate or (−)-cis-(3S)-amino-8-methyl-(5S)-phenyl-1,3,4,5-tetrahydro-benzo[b]azepine-2-one•(L)-(−)-dibenzoyltartarate, comprising reacting (D)-(+)-dibenzoyltartaric acid with either racemic or optically enriched cis-3-amino-8-methyl-5-phenyl-1,3,4,5-tetrahydro-benzo[b]azepine-2-one, or reacting (L)-(−)-dibenzoyltartaric acid with either racemic or enantiomerically enriched cis-3-amino-8-methyl-5-phenyl-1,3,4,5-tetrahydro-benzo[b]azepine-2-one in an organic solvent, preferably acetone or ethyl acetate.

Preferably, the diastereomeric salt (+)-cis-(3R)-amino-8-methyl-(5R)-phenyl-1,3,4,5-tetrahydro-benzo [b]azepine-2-one•(D)-(+)-dibenzoyltartarate or (−)-cis-(3S)-amino-8-methyl-(5S)-phenyl-1,3,4,5-tetrahydro-benzo[b]azepine-2-one•(L)-(−)-dibenzoyltartarate is neutralized to form, respectively, (+)-cis-(3R)-amino-8-methyl-(5R)-phenyl-1,3,4,5-tetrahydro-benzo[b]azepine-2-one or (−)-cis-(3S)-amino-8-methyl-(5S)-phenyl-1,3,4,5-tetrahydro-benzo[b]azepine-2-one.

Preferably, the diastereomeric salt (+)-cis-(3R)-amino-8-methyl-(5R)-phenyl-1,3,4,5-tetrahydro-benzo[b]azepine-2-one•(D)-(+)-dibenzoyltartarate or (−)-cis-(3S)-amino-8-methyl-(5S)-phenyl-1,3,4,5-tetrahydro-benzo[b]azepine-2-one•(L)-(−)-dibenzoyltartarate is neutralized with a base, preferably sodium hydroxide.

The present invention also relates to a process for the preparation of racemic compounds of formula

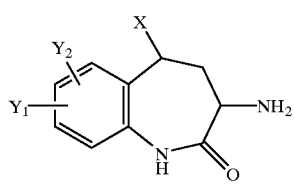

Ia wherein X and $NH_2$ are in the cis configuration in at least 90% of the molecules of formula Ia;

$Y^1$ and $Y^2$ are independently selected from halo, nitro, amino, $(C_1-C_6)$alkyl optionally substituted with from one to three fluorine atoms and $(C_1-C_6)$alkoxy optionally substituted with from one to three fluorine atoms; and X is selected from the group consisting of phenyl, $(C_3-C_8)$straight or branched alkyl and $(C_5-C_8)$cycloalkyl, wherein said phenyl may optionally be substituted with one or two substituents independently selected from the group consisting of halo, $(C_1-C_6)$alkyl, $(C_1-C_6)$alkoxy, nitro, amino and trifluoromethyl, and wherein said $(C_5-C_8)$cycloalkyl may optionally be substituted with one or two substituents independently selected from $(C_1-C_6)$alkyl; comprising reducing a compound of the formula

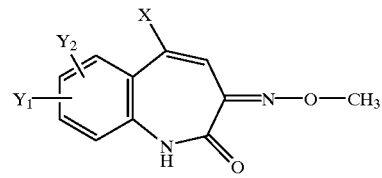

II wherein $Y^1$, $Y^2$ and X are defined as above, with Raney-nickel and a hydrogen source.

The present invention also relates to a process for the preparation of a compound of the formula

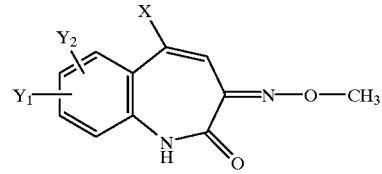

II wherein X, $Y^1$ and $Y^2$ are defined as above, comprising
a) reacting a compound of the formula

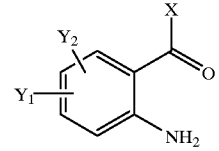

IV wherein X, $Y^1$ and $Y^2$ are defined as above, with a compound of formula

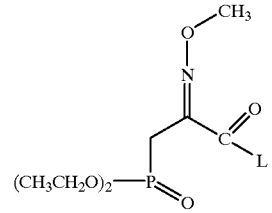

V wherein L is hydroxy, chloro, $-O_2COR$, and R is $(C_1-C_6)$alkyl, or L is a group of the formula

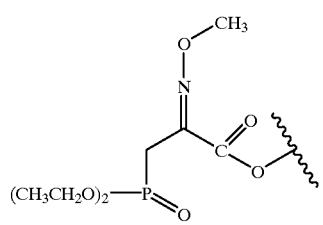

to form a compound of the formula

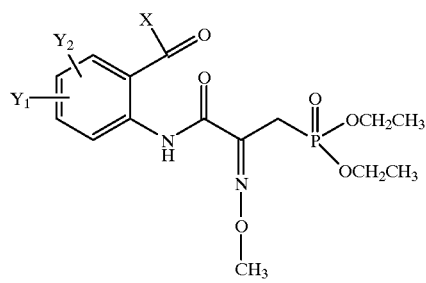

wherein X, $Y^1$ and $Y^2$ are defined as above, in an organic solvent, preferably dichloromethane;

and wherein said reaction is carried out in the presence of a dehydrating agent, preferably dicyclohexylcarbodiimide, 1-(3dimethylaminopropyl)-3-ethylcarbodiimide, or diphenylphosphoryl azide, when L is hydroxy;

and said reaction is carried out in the presence of an acid scavenger, preferably triethylamine, N-methyl-morpholine, dimethylaminopyridine or pyridine, when L is other than hydroxy; and b) reacting said compound of formula III, wherein X, $Y^1$ and $Y^2$ are defined as above, with a base, preferably potassium t-butoxide, in an organic solvent, preferably tetrahydrofuran.

DETAILED DESCRIPTION OF THE INVENTION

In the discussion and reaction schemes that follow, X, $Y^1$, $Y^2$ and L are as defined above.

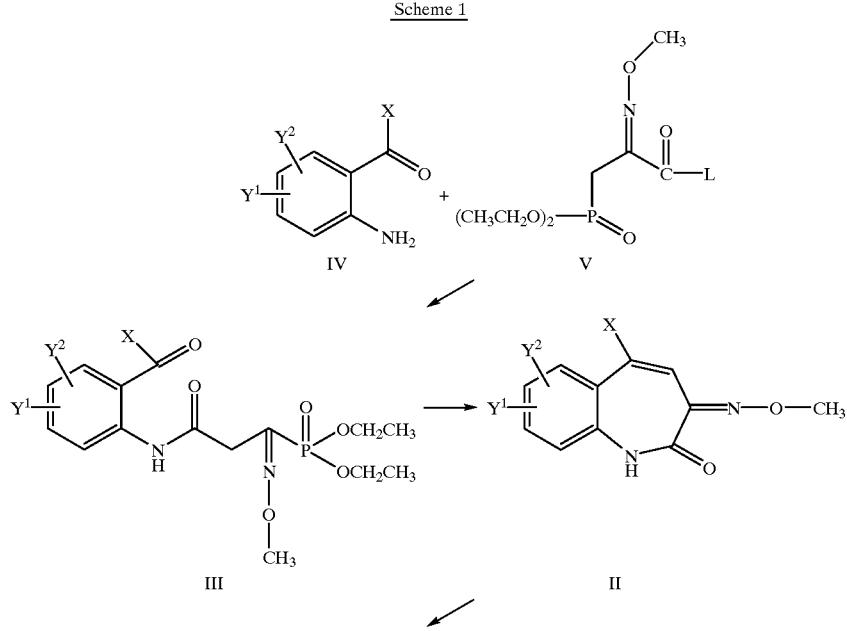

Scheme 1

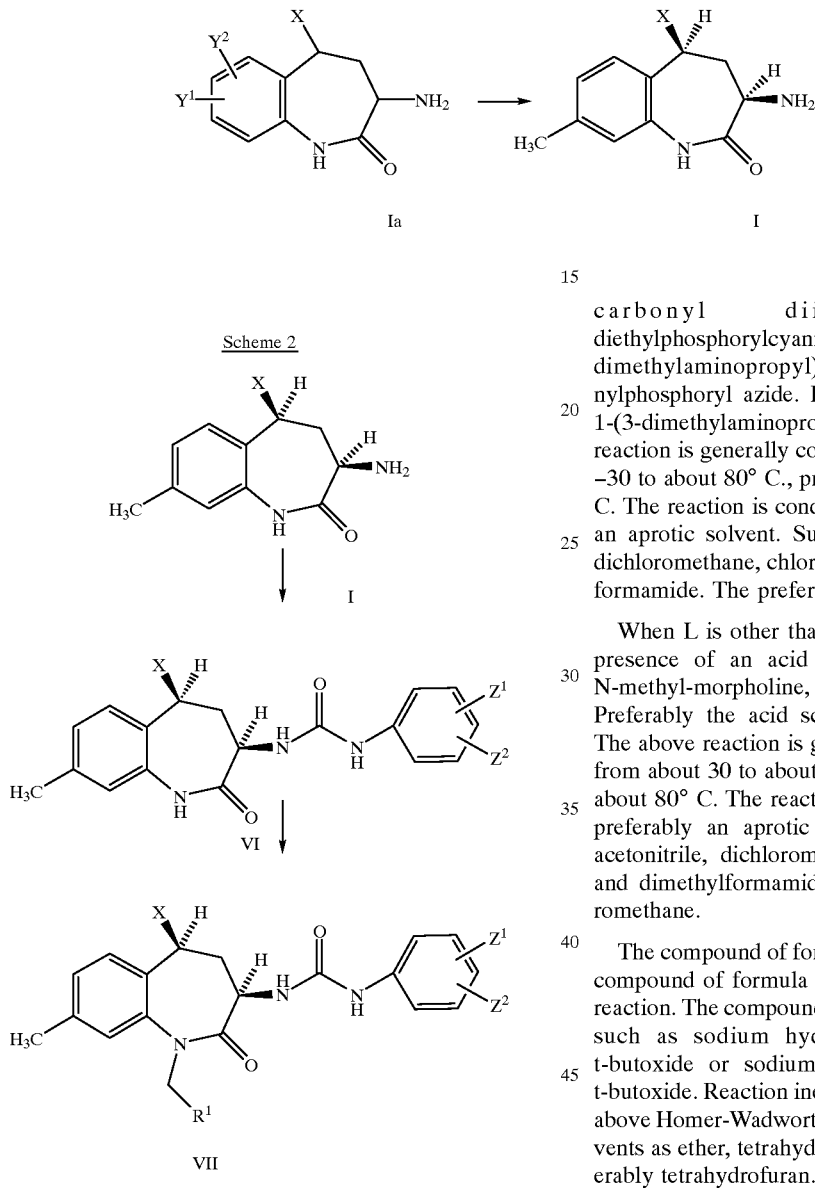

Scheme 2

The CCK intermediate (+)-cis-(3R)-amino-8-methyl-(5R)-phenyl-1,3,4,5tetrahydro-benzo[b]azepine-2-one of the invention has the formula I depicted in scheme 1 and can be prepared according to the methods described in scheme 1.

Referring to scheme 1, a compound of the formula IV is reacted with a compound of the formula V, wherein L is defined as above, in an organic solvent to form a compound of the formula III.

When L is hydroxy (—OH), then the reaction of the compound of formula IV with a compound of formula V requires the presence of a dehydrating agent which activates the carboxylic functionality of the acid for reaction with the amine. Examples of suitable dehydrating agents are dicyclohexylcarbodiimide/hydroxybenzo-triazole (HBT), N-(3-dimethylaminopropyl)-N'-ethylcarbodiimide/HBT, 2-ethoxy-1-ethoxycarbonyl-1,2-dihydroquinoline (EEDQ), carbonyl diimidazole (CDI)/HBT, diethylphosphorylcyanide, dicyclohexylcarbodiimide, 1-(3-dimethylaminopropyl)-3-ethylcarbodiimide, and diphenylphosphoryl azide. Preferably, the dehydrating agent is 1-(3-dimethylaminopropyl)3ethylcarbodiimide. The above reaction is generally conducted at a temperature from about −30 to about 80° C., preferably from about 20 to about 80° C. The reaction is conducted in an inert solvent, preferably an aprotic solvent. Suitable solvents include acetonitrile, dichloromethane, chloroform, dichloroethane and dimethylformamide. The preferred solvent is dichloromethane.

When L is other than hydroxy, the reaction requires the presence of an acid scavenger such as triethylamine, N-methyl-morpholine, dimethylaminopyridine or pyridine. Preferably the acid scavenger is dimethylaminopyridine. The above reaction is generally conducted at a temperature from about 30 to about 80° C., preferably from about 20 to about 80° C. The reaction is conducted in an inert solvent, preferably an aprotic solvent. Suitable solvents include acetonitrile, dichloromethane, chloroform, dichloroethane and dimethylformamide. The preferred solvent is dichloromethane.

The compound of formula III is cyclized to a benzazepine compound of formula II by a Homer-Wadsworth-Emmons reaction. The compound of formula III is treated with a base, such as sodium hydride, sodium amide, potassium t-butoxide or sodium methoxide, preferably potassium t-butoxide. Reaction inert solvents that are acceptable for the above Homer-Wadworth-Emmons reaction include such solvents as ether, tetrahydrofuran, or dimethylformamide preferably tetrahydrofuran. The reaction is performed at a temperature of from about 20° C. to about 70° C., preferably from about 40° C. to about 70° C.

The compound of formula IV so formed is then reduced to a racemic amine of formula Ia via olefin hydrogenation using a transition metal catalyst and a hydrogen source in an inert solvent. The compound of formula Ia so formed encompasses a mixture of four isomers including two cis isomers (formula I and I' below) and two trans isomers. The trans isomers are not shown. The two cis isomers (wherein X and $NH_2$ are on the same side of the benzazepine ring) comprise in excess of 90% of the molecules formed in the reduction. Preferably, the two cis isomers (wherein X and $NH_2$ are on the same side of the benzazepine ring) comprise in excess of 95% of the molecules formed in the reduction. The trans isomer accounts for less than 10% of the reaction product, preferably less than 5%. The cis compounds of formula Ia consist of compounds of the formula

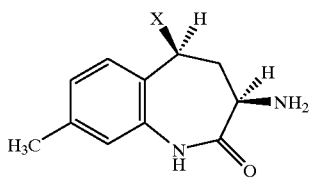

and

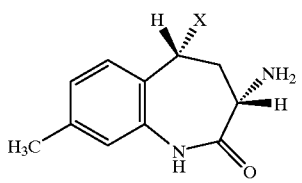

Suitable transition metal catalysts that are useful for the reduction include palladium on carbon, palladium hydroxide on carbon, tetrakis(triphenylphoshine)palladium(O), Raney-Nickel and rhodium(II) acetate. The preferred transition metal catalyst is Raney-Nickel. Suitable hydrogen sources include hydrogen gas, ammonium formate, and formic acid. The preferred hydrogen source is hydrogen gas, preferably used at a pressure from about one to about three atmospheres. Suitable inert solvents include ($C_1$ to $C_4$) alcohols, N,N-dimethylformamide, ethyl acetate, and acetic acid. The preferred solvent is methanol. The reaction is generally run at a temperature from about 20° C. to about 75° C., preferably at a temperature from about 20° C. to about 30° C.

The racemic amine of formula Ia, wherein X is phenyl, $Y^1$ is 8-methyl, and $Y^2$ is hydrogen can be resolved to yield the (3R, 5R) and (3S, 5S) isomers of formula I by formation of an amine salt with (D)-(+)-dibenzoyltartaric acid or (L)-(−)-dibenzoyltartaric acid in an appropriate solvent. The racemic amine of formula Ia, wherein X is phenyl, $y^1$ is 8-methyl and $Y^2$ is hydrogen, can be resolved by recrystallizing the racemate of formula Ia with either (D)-(+)-dibenzoyltartaric acid or (L)-(−)-dibenzoytartaric acid in an organic solvent to yield a diastereomeric salts of the formula

A

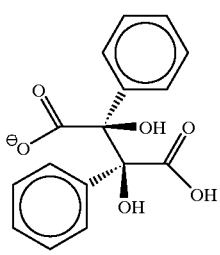

and

B

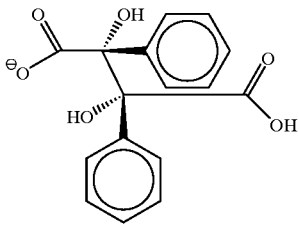

wherein X is phenyl. The salt so formed may be repeatedly recrystallized from the same or different solvent or may be directly converted to the pure enantiomer of formula I wherein X is phenyl.

Appropriate solvents for the foregoing resolutions of the (3R, 5R) and (3S, 5S) isomers of formula I include any solvent capable of dissolving the reactants and selectively dissolving one of the two diastereomeric salts formed, while causing the other to precipitate out of solution. Examples of such solvents are acetone and ethyl acetate. The preferred solvent is acetone. The temperature of the foregoing resolution is from about 0° C. to about 100° C., preferably at about room temperature. The initial salt may contain small amounts of the undesired diasteriomer salt.

A second crystallization can be performed by dissolving the enantiomerically enriched diastereomeric salt of formula A or B, depicted above, in hot methanol, adding ethyl acetate to give a precipitate and finally distilling out most of the methanol while maintaining the volume by addition of fresh ethyl acetate. The final slurry is then cooled to room temperature and the pure salt of formula A or B wherein X is phenyl is collected by filtration.

When (D)-(+)-dibenzoyltartarate is used as the resolving agent, as described above, the (D)-(+)-dibenzoyltartarate salt (+)-cis-(3R)-amino8-methyl-(5R)-phenyl-1,3,4,5tetrahydro-benzo[b]azepine-2-one precipitates out of solution and can be physically separated and purified by methods well known to those skilled in the art. The (D)-(+) dibenzoyltartarate salt of the opposite enantiomer (−)-cis-(3S)-amino-8-methyl-(5S)-phenyl-1,3,4,5tetrahydro-benzo[b]azepine-2-one remains in solution. When (L)-(−)-dibenzoyltartarate is used as the resolving agent, (−) -cis-(3S)-amino-8-methyl-(5S)-phenyl-1,3,4,5tetrahydro-benzo[b]azepine-2-one precipitates out of solution, while (+)-cis-(3R)-amino-8-methyl-(5R)-phenyl-1,3,4,5-tetrahydro-benzo[b]azepine-2-one remains in solution.

Neutralization of the dibenzoyltartarate salts of (+)-cis-(3R)-amino-8-methyl-(5R)-phenyl-1,3,4,5-tetrahydro-benzo[b]azepine-2-one•(D)-(+)-dibenzoyltartarate or (−)-cis-(3S)-amino-8-methyl-(5S)-phenyl-1,3,4,5-tetrahydro-benzo[b]azepine-2-one•(L)-(+)-dibenzoyltartarate to form the corresponding optically active free amines may be accomplished using methods well known in the art.

For example, such neutralization may be accomplished by reacting the dibenzoyttartarate salts with a base such as sodium hydroxide, potassium hydroxide, sodium carbonate or potassium carbonate. Suitable solvents for the neutralization step include chlorohydrocarbons, ethers, benzene, toluene and water, as well as mixtures of the foregoing solvents (e.g., diethyl ether, diisopropyl ether, methylene chloride, or methylene chloride/water). Suitable temperatures range from about 15° C. to about 100° C., with room temperature (30° C.) being preferred.

The compound of the formula I can be converted into compounds of the formula VII, which are CCK antagonists, according to the methods of scheme 2. The processes of scheme 2 are described in detail in PCT Patent Publication WO93/15059 published Aug. 5, 1993 which is hereby incorporated by reference in its entirety.

Referring to scheme 2, the compound of formula I is converted into the corresponding compound having formula VI by reacting it with an isocyanate of the formula $C_6H_4Z^1Z^2NCO$, wherein $Z^1$ and $Z^2$ are independently selected from the group consisting of halo, $(C_1-C_6)$ alkyl, $(C_1-C_6)$ thioalkyl, $(C_1-C_6)$ alkoxy, trifluoromethyl, $(C_1-C_6)$ carboalkoxy, amino and nitro. Appropriate reaction inert solvents for this reaction include hydrocarbons such as hexane, benzene and toluene, halogenated hydrocarbons such as methylene chloride and 1,2-dichloroethane, ethereal solvents such as ethyl ether, tetrahydrofuran (THF) and glyme, and pyridine. The preferred solvent is 1,2-ichloroethane or methylene chloride. Tertiary organic amines may be useful as catalysts. The reaction temperature may range from about 0° C. to about 150° C. The reflux temperature is preferred.

The isocyanate of the formula $C_6H_4Z^1Z^2NCO$ used in the foregoing reaction can be formed by procedures well known to those skilled in the at or are commercially available. One such method involves mixing a benzoic acid derivative with diphenylphosphorylazide, or an analogous reagent, in the presence of an organic base such as a trialkylamine, preferably triethylamine or diisopropylethylamine. This reaction is usually conducted in an ethereal, hydrocarbon or chlorinated hydrocarbon solvent, preferably tetrahydrofuran or benzene, at a temperature from about room temperature to about 100° C., preferably at the reflux temperature of the solvent, for a period from about 20 minutes to about 24 hours, preferably about 1 hour.

The compound of formula VI is then alkylated at the ring nitrogen by reaction with a compound of the formula $L'CH_2R^1$, wherein $L'$ is bromine or iodine and $R^1$ is $CO_2R^2$, $SO_2NR^3R^6$ or $CONR^4R^5$, and wherein $R^2$, $R^3$, $R^4$, $R^5$ and $R^6$ are independently selected from hydrogen, $(C_3-C_{12})$ alkyl and fused, saturated carbocyclic systems containing two or three rings and phenyl, wherein said phenyl may optionally be substituted with one or two substituents independently selected from halo, $(C_1-C_6)$ alkyl, $(C_1-C_6)$ alkoxy, nitro, amino and trifluoromethyl; and wherein $L'$ is bromine when $R^1$ is phenyl or substituted phenyl, and L is iodine when $R^1$ is $—CO_2R^2$, $—SO_2NR^3R^6$ or $—CONR^4R^5$; in tetrahydrofuran (THF) in the presence of solid potassium hydroxide and a catalytic amount of tetra-n-butyl ammonium bromide. This reaction, which yields the corresponding compound of formula VII, is usually conducted at a temperature from about 25° C. to about 35° C. It is preferably conducted at room temperature (30° C.) .

The compounds of the formula VII which are basic in nature are capable of forming a wide variety of different salts with various inorganic and organic acids. Although such salts must be pharmaceutically acceptable for administration to animals, it is often desirable in practice to initially isolate a compound of the formula I or II from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of formula VII and their pharmaceutically acceptable salts (hereinafter referred to collectively as "the active compounds") are useful as selective CCK-B receptor antagonists, i.e., they possess the ability to antagonize the effects of CCK at its B receptor site in mammals, and therefore they are able to function as therapeutic agents in treating or preventing pain, gastrointestinal disorders such as ulcer and colitis, and central nervous system disorders such as anxiety and panic disorders in an afflicted mammal.

The active compounds can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The active compounds may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

The activity of the active compounds as CCK-B antagonists may be determined by an assay that measures their ability to inhibit the binding of 125-I-BH-CCK-8 to the CCK-B receptor in a guinea pig cortical membrane preparation. This procedure is carried out as follows. The cortex is dissected from one male Hartley Guinea pig and homogenized (15 strokes) with a teflon homogenizer in 20 volumes (w./v.) of the assay buffer, which consists of 50 mM Tris (i.e., trimethamine, which is 2-amino-2-hydroxymethyl-1, 3propanediol) hydrochloric acid having pH 7.4 and 5 mM of manganese chloride at 4° C. The homogenate is centrifuged at 4° C. for 30 minutes at 100,000×G. The pellet is resuspended in the same buffer and spun as described above. The final pellet is diluted to a concentration of 20 mg/ml with the assay buffer for use in the binding assay. The tissue is kept on ice at all times.

An incubation mixture is prepared, which consists of 50 uL of the tissue preparation, prepared as described above, 100 uL 125-I-BH-CCK-8 (to give a concentration of 50 pM in the final assay), 20 uL of a blank or the compound being tested, and 30 uL of Tris with 4% dimethylsulfoxide (DMSO). All drugs and dilutions are made using 4% DMSO in the assay buffer yielding a final assay DMSO concentration of 1%.

The reaction is initiated with the addition of tissue to a 96-well plate containing 125-I-BH-CCK-8 and the appropriate blank or compound being tested. Non-specific binding is estimated using 1 uM sulphated CCK-8. The reaction is terminated by spinning the plates in a H1000B rotor fitted on a Sorvall RT6000 refrigerated centrifuge at 4° C. The supernatant is discarded, and the pellets washed with 200 uL of assay buffer, and the plate is spun as above. The supernatant is decanted again, and the pellet is harvested onto Betaplate filters (which have been soaked in 0.2% polyethyleneimine for a minimum of 2 hours) using a Skatron cell harvester at setting 222 using Tris HCl pH 7.4 as the wash buffer. The filtermats are counted on a Betaplate counter for 45 seconds per sample.

Data are expressed as $IC_{50}$ values (the concentration which inhibits 50% of the specific binding of 125-I-BH-CCK-8). The data is analyzed using non-linear regression analysis.

The following Examples illustrate the preparation of the intermediates of the present invention. Commercial reagents were utilized without further purification. Melting points are uncorrected. NMR data are reported in parts per million (d) and are referenced to the deuterium lock signal from the sample solvent. Specific rotations were measured at room temperature using the sodium D line (589 nm). Unless otherwise stated, all mass spectra were performed using electron impact (EI, 70 eV) conditions. Chromatography refers to column chromatography performed using 32–63 μm silica gel and executed under nitrogen pressure (flash chromatography) conditions. Room temperature refers to 20–25° C.

EXAMPLE 1

(+)-Cis-(3R)-amino-8-methyl-(5R)-phenyl-1,3,4,5-tetrahydro-benzo[b]azepine-2-one:

A. Ethyl 3-bromo-2-(methoxyimino)-propionate:

Ethyl bromopyruvate (50 g, 0.23 mol) and methoxylamine hydrochloride (23.2 g, 0.27 mol) were dissolved in 2B ethanol (185 ml) at 35° and stirred overnight. Most of the alcohol was then evaporated in vacuo to provide a semisolid which was taken up in methylene chloride (300 ml) and 0.5 M HCl. The organic layer was separated and washed a second time with 0.5 M HCl followed with a brine wash and then dried over magnesium sulfate. Filtration and evaporation in vacuo provided the oxime ester as a yellow oil; 48.1 g, 93% yield. This was used without further purification.

B. Triethyl 3-phosphono-2-(methoxyimino)-propionate:

Ethyl 3-bromo-2-(methoxyimino)-propionate (48 g, 0.214 mol) and triethyl phosphite (35.5 g, 0.214 mol) were combined and heated under a nitrogen atmosphere to 150–155° C. for 5 hours. The reaction was cooled to room temperature. $^1$H NMR showed the resulting oil to be largely the desired phosphonate. This was used as is in the following hydrolysis step. $^1$H NMR (chloroform-d, $CDCl_3$) δ 4.29 (q, 2), 4.05 (m and s, 7), 3.25 (d, 2, J=24 Hz), 1.25 (m, 9).

C. Diethyl 3-phosphono-2-(methoxyimino)-propionic acid:

Sodium hydroxide 1N NaOH (45 ml, 45 mmol) was added to a solution of triethyl 3-phosphono-2-(methoxyimino)-propionate (11.6 g, 41 mmol) in ethanol (30 ml) and the reaction was stirred at room temperature for 5 hours. The reaction mixture was then extracted twice with ether, then acidified with 1N HCl (50 ml) and extracted 3 times with methylene chloride. The methylene chloride layers were combined, washed with brine, and dried over sodium sulfate. Filtration of the drying agent and evaporation in vacuo provided the acid, as an oil which crystallized upon refrigeration. This was used without further purification. $^1$H NMR ($ODCl_3$) δ 9.20 (s, 1, $CO_2H$), 4.20–4.05 (m, 7), 3.34 (d, 2, J=24 Hz), 1.30 (t, 6).

D. 2-(Diethyl 3-phosphono-2-(methoxyimino)-propionamidoyl)-4-methylbenzophenone:

Diethyl 3phosphono-2-(methoxyimino)-propionic acid (1.7 g, 7.17 mmol), 2-amino-4-methylbenzophenone (1 g, 5 mmol) and 1-(3-dimethylaminopropyl)-3-ethylcarbodiiminde hydrochloride (1.5 g, 7.8 mmol) were refluxed in methylene chloride (20 ml) for 8 hours. The reaction was then washed with water, 2N hydrochloric acid (HCl), aqueous sodium bicarbonate and brine. The solution was dried over magnesium sulfate and evaporated in vacuo to an oil. This oil was purified by column chromatography through silica gel with an eluant of 5% ethyl acetate in chloroform to remove unreacted benzophenone. The product was isolated as a crystalline solid, 0.91 g, 41%. mp 115–18° C. $^1$H NMR ($CDCl_3$) δ 11.97 (s, 1), 8.59 (s, 1), 7.70–7.42 (m, 6), 6.90 (d, 1), 4.19 (s, 3), 4.13 (q, 4), 3.40 (d, 2, J=24 Hz). 2.42 (s, 3) 132 (t, 6).

E. 8-Methyl-5-phenyl-1 H-benzo[b]azepine-2,3dione 3(O-methyl-oxime):

2-(Diethyl 3-phosphono-2-(methoxyimino)-propionamidoyl)-4-methyl-benzophenone (17.6 g, 39.5 mmol) was dissolved in tetrahydrofuran (160 ml) at room temperature under a nitrogen atmosphere. The reaction was cooled with ice water to 4° C. and potassium t-butoxide (9.32 g, 79 mmol) was added in one portion. The cooling bath was removed and the reaction was heated to reflux for 0.5 hours. The reaction was once again cooled and then diluted with ethyl acetate (100 ml) and washed with water and brine. After drying over magnesium sulfate, the solvent was evaporated in vacuo to afford a solid that was crystallized from isopropanol; 10 g, 87% yield, mp 234–370° C. $^1$H NMR ($CDCl_3$) δ 9.71 (s, 1 NH), 7.38 (bs, 5), 7.05 (s, 1), 6.96 (d, 1, J=8.1 Hz), 6.84 (d, 1, J=8.1 Hz), 6.67 (s, 1, vinyl), 4.13 (s, 3, $NOCH_3$) 235 (s, 3). $^{13}$C NMR ($CDCl_3$) δ 167.53, 149.09, 144.69, 141.73, 140.33, 135.03, 131.45, 129.14, 128.50, 128.43, 126.14, 125.13, 122.26, 118.68, 63.62, 21.08. Analysis Calculated for $C_{18}H_{16}N_2O_2$: C, 73.96; H, 5.52; N, 9.58. Found: C, 74.22; H, 5.69; N, 9.52. The structure was confirmed by single crystal X-ray analysis.

F. Cis-3-Amino-8-methyl-5-phenyl-1,3,4,5-tetrahydro-benzo[b]azepine-2-one:

Raney-nickel (Aldrich Chem., 40 g of aqueous slurry) washed once with water and three times with methanol (each time the excess solvent was drawn off by syringe under nitrogen) was diluted with a slurry of 8-methyl-5phenyl-1, 3,4,5-tetrahydro-benzo[b]azepine-2,3-dione 3(O-methyl-oxime) (10 g, 34 mmol) in methanol to produce a final volume of about 600 ml. The reaction was shaken at 50 psi hydrogen pressure for 24 hours. Thin layer chromatography of an aliquot showed the reduction was complete at this point. The hazy solution was twice filtered through Celite® to give a clear solution which was evaporated in vacuo to provide the amine as a white solid; 8 g, 88% yield. $^1$H NMR ($CDCl_3$) δ 7.52 (s, 1), 7.80–7.05 (m, 6), 6.96 (d, 1), 6.71 (s, 1), 4.30 (q, 1), 3.61 (q, 1), 2.82 (m, 1), 2.50 (m, 1), 2.32 (s, 3) 1.70 (bs, 2, $NH_2$).

G. (+)-Cis-(3R)-Amino-8-methyl-(5R)-phenyl-1,3,4,5-tetrahydro-benzo[b]azepine-2-one (+)-dibenzoyltartarate:

Cis-3-Amino-8-methyl-5-phenyl-1,3,4,5-tetrahydro-benzo[b]azepine-2-one (7.81 g, 29 mmol) and D-(+)-dibenzoyltarteric acid (10.5 g, 29.3 mmol) were combined in acetone (300 ml) and stirred at room temperature. This initially gave a clear solution followed by crystallization. After stirring for 4 hours, the solids were collected, washed with acetone and dried in vacuo at 40° C. to produce 7.89 grams of a salt. This initial salt (6.74 g) was dissolved in methanol (75 ml) with heating to give a clear solution. Ethyl acetate (205 ml) was added to the hot solution over 5 minutes to cause crystallization. A total of 280 ml of distillate was collected at atmospheric pressure, while adding additional ethyl acetate to maintain the original volume. The slurry was allowed to cool to room temperature over one hour and the solids were collected and washed with ethyl acetate. The yield of the recrystallization was 6.2 g, 92% or 40% for the overall resolution. The material was a white solid, mp 193–4° C. (dec.).[$\alpha_D$] 180.6° (c=0.205, methanol, MeOH). The structure and absolute configuration was determined by a single crystal X-ray analysis.

H. (+)-Cis-(3R)-amino-8-methyl-(5R)-phenyl-1,3,4,5-tetrahydro-benzo[b]azepine-2-one:

The dibenzoyl tartarate salt (6.98 g, 11.2 mmol) was dissolved in a mixture of 0.5N NaOH and methylene chloride (50 ml). The layers were separated and the aqueous layer was extracted with methylene chloride (30 ml). The organic layers were combined, washed with water, and dried over magnesium sulfate. This was filtered and concentrated in vacuo to about 25 ml at which point hexanes (50 ml) were added slowly. This process was repeated with more hexanes and the product was collected and dried in vacuo; 2.9 g, 98% yield. [$\alpha_D$] 259.5° (c=0.264, MeOH). $^1$H NMR (CDCl$_3$) same as racemic amine. $^{13}$C NMR (CDCl$_3$)δ 177.0, 143.5, 138.0, 135.8, 133.1, 131.6, 128.3, 127.2, 126.6, 126.2, 123.7, 61.1, 51.3, 45.8, 42.0, 20.9.

EXAMPLE 2

Cis-3-Amino-5-cyclohexyl-1,3,4,5-tetrahydro-benzo[b]azepine-2-one:

D. {2-[2-(Cyclohexylcarbonyl)-phenylcarbamoyl]-2-methoxyimino-ethyl}-phosphonic acid diethyl ester:

The title compound was prepared from the readily available phenone according to the methods of procedures A through D of Example 1.

Yield 5.65 g, 66%. mp 96–8° C. IR (potassium bromide, KBr) 1682, 1655 cm$^{-1}$. $^1$H NMR (CDCl$_3$) δ 12.56 (s, 1), 8.77 (d, 1), 7.92 (d, 1), 7.54 (t, 1), 7.15 (t, 1), 4.22 (s, 3) 4.14 (m, 4), 3.40 (d, 2), 3.30 (m, 1), 1.92–1.20 (m, 11).

E. 5-Cyclohexyl-1 H-benzo[b]azepine-2,3-dione 3-(O-methyl-oxime):

The title compound was prepared from the produce of step D described above in a method analogous to procedure E in Example 1.

Yield 1.7 g, 53%. mp 192–200° C. IR (KBr) 1675, 1629 cm$^{-1}$. $^1$H NMR (CDCl$_3$) δ 9.50 (s, 1), 7.50 (d, 1), 7.39 (t, 1), 7.29 (m, 2), 6.40 (s, 1), 4.04 (s, 3), 269 (bt, 1), 195–1.70 (m, 5), 1.47–1.18 (m, 5). $^{13}$C NMR (CDCl$_3$) δ 168.6, 149.6, 148.8, 134.5, 129.9, 129.0, 127.1, 124.6, 122.6, 116.8, 63.42, 43.1, 33.23, 26.7, 26.2. Mass spectrum: m/e 285 (M+1). Analysis Calculated for C$_{17}$H$_{20}$N$_2$O$_2$: C, 71.81; H, 7.09; N, 9.85. Found: C, 71.80; H, 7.37; N, 9.96.

F. Cis-3-Amino-5-cyclohexyl-1,3,4,5-tetrahydro-benzo[b]azepine-2-one:

Under similar hydrogenation conditlons as described above in method F of Example 1, the product of step E was reduced to the title compound.

Yield 0.78 g, 86%. $^1$H NMR (CDCl$_3$) δ 7.68 (s, 1), 7.27–7.18 (m, 1), 7.10 (d, 2), 6.92 (d, 1), 3.50 (q, 1), 2.63–2.49 (m, 2), 2.01 (m, 2), 1.78–147 (m, 6) 1.30–0.78 (m, 5), 0.55 (m, 1).

EXAMPLE 3

Cis-3-Amino-5-cyclohexyl-8-methyl-1,3,4,5-tetrahydro-benzo[b]azepine-2-one:

D. {2-[2-(Cyclohexylcarbonyl)-5-methyl-phenylcarbamoyl]-2-methoxyimino-ethyl}-phosphonic acid diethyl ester:

The title compound was prepared from the readily available phenone according to the methods of procedures A through D in Example 1.

Yield 3.14 g, 52%. mp 64–6° C. IR (KBr) 1680, 1643, 1612, 1570, 1530 cm$^{-1}$. $^1$H NMR (CDCl$_3$) δ 12.66 (s, 1), 8.63 (d, 1), 6.93 (d, 1), 4.20 (s, 3), 4.12 (q, 4), 3.39 (d, 2), 3.28 (m, 1), 2.38 (s, 3), 1.90–1.19 (m with t at 1.27, 16). $^{13}$C NMR (CDCl$_3$) δ 207.0, 161.0, 146.0, 145.8, 145.5, 140.4, 130.5, 123.5, 121.5, 119.6, 63.6, 62.3, 62.2, 61.0, 46.5, 29.7, 25.9, 25.8, 23.6, 22.1, 21.8, 16.3, 16.2. Analysis Calculated for C$_{22}$H$_{33}$N$_2$O$_6$P: C, 58.40; H, 7.35; N, 6.19. Found: C, 58.44; H, 7.46; N, 6.24.

E. 8-Methyl-5-cyclohexyl-1H-benzo[b]azepine-2,3-dione 3-(O-methyl-oxime):

The title compound was prepared from the product of step D, described above, in a method analogous to procedure E in Example 1.

Yield 0.41 g, 52%. mp 222–226° C. IR (KBr) 1679, 1631, 1617, 1563. cm$^{-1}$. $^1$H NMR (CDCl$_3$) δ 9.53 (s, 1), 7.49 (d, 1), 6.99 (m, 2), 6.34 (s, 1), 4.02 (s, 3), 2.66 (t, 1), 2.33 (s, 3), 1.91–1.69 (m, 5), 1.44–1.12 (m, 5). $^{13}$C NMR (CDCl$_3$) δ 168.4, 149.8, 148.8, 139.3, 134.3, 127.1, 125.6, 122.7, 116.0, 89.0, 63.4, 43.0, 33.2, 26.8, 26.2, 20.9. Mass spectrum: m/e 298 (M$^+$), 267 (M$^+$-OMe). Analysis Calculated for C$_{18}$H$_{22}$N$_2$O$_2$: C, 72.46; H, 7.43; N, 9.39. Found: C, 72.42; H, 7.51; N, 9.45.

F. Cis-3-Amino-5-cyclohexyl-8-methyl-1,3,4,5-tetrahydro-benzo[b]azepine-2-one:

Under similar hydrogenation conditions as described above in method F of Example 1, the product from step E was reduced to the title compound.

Yield 0.22 g, 79%. $^1$H NMR (CDCl$_3$) δ 8.03 (s, 1), 6.99 (d, 1), 6.90 (d, 1), 6.75 (s, 1), 3.50 (q, 1), 2.61–2.42 (m, 2), 2.30 (s, 3), 1.98 (m, 2), 1.78–145 (m,6), 126–0.73 (m, 5), 0.51 (m, 1).

EXAMPLE 4

5-Methyl-1H-benzo[b]azepine-2,3-dione-3-(O-methyl-oxime):

D. 2-(Diethyl 3-phosphono-2-(methoxyimino)-propionamidoyl)-acetophenone:

The title compound was prepared from the readily available phenone according to the methods of procedures A through D from Example 1.

Yield 1.5 g, 41%. $^1$H NMR (CDCl$_3$) δ 12.62 (s, 1), 8.79 (d, 1), 7.89 (d, 1), 7.55 (t, 1), 7.11 (t, 1), 4.19 (s, 3), 4.10 (m, 4), 3.40 (d, 2, J=25 Hz), 2.66 (s, 3), 1.27 (t, 6).

E. 5-Methyl-1H-benzo[b]azepine-2,3-dione-3-(O-methyl-oxime):

The title compound was prepared from the product from step D, described above, in a method analogous to procedure E in Example 1.

Yield 0.45 g, 52%. mp 190–3° C. IR (KBr) 1669, 1630 cm$^{-1}$. $^1$H NMR (CDCl$_3$) δ 9.61 (s, 1), 7.48 (d, 1), 7.33–7.13 (m, 3), 6.54 (s, 1), 4.06 (s, 3), 2.35 (s, 3) $^{13}$C NMR (CDCl$_3$) δ 167.3, 148.7, 139.5, 134.2, 129.6, 129.0, 127.8, 124.4, 122.3, 118.7, 63.5, 23.8. Mass spectrum: m/e 217 (M+1). Analysis Calculated for C$_{12}$H$_{12}$N$_2$O$_2$: C, 66.65; H, 5.59; N, 12.95. Found: C, 66.71; H, 5.72; N, 13.05.

EXAMPLE 5

Cis-3-Amino-7.8-dimethoxy-5-methyl-1,3,4,5-tetrahydro-benzo[b]azepine-2-one:

D. 2-(Diethyl-3-phosphono-2-(methoxyimino)-propionamidoyl)-4,5-dimethoxy-acetophenone:

The title compound was prepared from the readily available phenone according to the methods of procedures A through D in Example 1.

Yield 4.62 g, 75%. mp 103° C. IR (KBr) 1675, 1646, 1609, 1586 cm$^{-1}$. $^1$H NMR (CDCl$_3$) δ 12.88 (s, 1), 8.56 (s, 1), 7.29 (s, 1), 4.20 (s, 3), 4.20 (q, 4), 3.99 (s, 3), 3.90 (s, 3), 3.40 (d, 2), 2.61 (s, 3), 1.28 (t, 6). Analysis Calculated for C$_{18}$H$_{27}$N$_2$O$_6$P: C, 50.23; H, 6.32; N, 6.51. Found: C, 50.36; H, 6.37; N, 6.73.

E. 5-Methyl-7,8-dimethoxy-1H-benzo[b]azepine-2,3-dione 3-(O-methyl-oxime):

The title compound was prepared from the product of step D described above in a method analogous to procedure E in Example 1.

Yield 1.68 g, 52%. mp 233–35° C. IR (KBr) 1659, 1627, 1615, 1583 cm$^{-1}$. $^1$H NMR (CDCl$_3$) δ 9.80 (s, 1), 6.88 (s, 1), 6.73 (s, 1), 6.41 (s, 1), 4.00 (s, 3) 3.90 (s, 3), 3.85 (s, 3), 2.31 (s, 1). $^{13}$C NMR (CDCl$_3$) δ 166.9, 149.9,148.8, 145.6, 139.1, 128.5, 121.5, 117.1, 110.0, 105.2, 63.3, 56.2, 56.1, 23.9. Analysis Calculated for C$_{14}$H$_{16}$N$_2$O$_4$: C, 60.85; H, 5.84; N, 10.14. Found: C, 61.07; H, 5.91; N, 10.34.

F. Cis-3-Amino-7.8-dimethoxy-5-methyl-1,3,4,5-tetrahydro-benzo[b]azepine-2-one:

Under similar hydrogenation conditions as described above in method F of Example 1, the product from step E above was reduced to the title compound.

Yield 73%. $^1$H NMR (CDCl$_3$) δ 7.60 (s, 1), 6.69 (s, 1), 6.50 (s, 1), 3.88 (s, 3), (s, 3), 3.49 (q, 1), 3.00 (m, 1), 2.74 (m, 1), 1.71 (dt, 1), 1.60 (bs, 2), 1.30 (d, 3)

EXAMPLE 6

Cis-6-Amino-7,7a-dihydro-4H,6H-fluoreno-[1,9-bc]azepine-5-one:

D. 1-(Diethyl 3-phosphono-2-(methoxyimino)-propionamidoyl)-fluorenone:

The title compound was prepared from the readily available phenone according to the methods of procedures A through D in Example 1.

Yield 1.68 g, 39%. mp 104–7° C. IR (KBr) 1695, 1653, 1614, 1602 cm$^{-1}$. $^1$H NMR (CDCl$_3$) δ 11.25 (s, 1), 8.41 (d, 1), 7.62 (d, 1) 7.51–7.41 (m, 3), 7.28 (dt, 1) 7.20 (d, 1), 4.24 (s, 3), 4.11 (m, 4), 3.40 (d, 2, J=25 Hz), 1.29 (t, 6).

E. 4H-Fluoreno[1,9-bc]azepine-5,6-dione6-(O-methyl-oxime):

The title compound was prepared from the phosphonate amide described in step D above in a method analogous to procedure E in Example 1.

Yield 0.59 g, 61%. mp 254–61° C. IR (KBr) 1681, 1667, 1637, 1615 cm$^{-1}$. $^1$H NMR (CDCl$_3$) δ 8.75 (s, 1), 7.70 (d, 1), 7.75 (s, 1), 7.69 (d, 1), 7.46–7.31 (m, 4) 6.82 (d, 1), 4.28 (s, 3). $^{13}$C NMR (CDCl$_3$) δ 160.7, 149.1, 140.9, 140.0, 139.3, 137.4, 134.8, 132.3, 130.6, 128.4, 122.4, 122.2, 121.2, 118.1, 115.7, 110.0, 63.8. Analysis Calculated for C$_{17}$H$_{12}$N$_2$O$_2$: C, 73.90; H, 4.38; N, 10.14. Found: C, 74.05; H, 4.51; N, 10.40.

F. Cis-6-Amino-7,7a-dihydro-4H,6H-fluoreno[1,9-bc]azepine-5-one:

Under similar hydrogenation conditions as described above in method F of Example 1, the product from step E above was reduced to the title compound.

Yield 0.29 g, 80%. $^1$H NMR (CDCl$_3$) δ 7.88 (s, 1), 7.75 (d, 1), 7.60 (d, 1), 7.49–7.30 (m, 4), 6.93 (d, 1), 4.10 (t, 1), 3.61 (q, 1), 2.71 (q, 1), 2.40 (m, 1), 1.70 (bs, 2).

PREPARATION 9

A. (+)-3(R)-[3-(3-Chloro-phenyl)-ureido]-8-methyl-2-oxo-5(R)-phenyl-1,3,4,5-tetrahydro-benzo[b]azepine:

(+)-Cis-(3R)-amino-8-methyl-(5R)-phenyl-1,3,4,5-tetrahydro-benzo[b]azepine-2-one (2 g, 7.52 mmol) was suspended in 1,2-dichloroethane (40 ml) and stirred under nitrogen while 3-chlorophenyl isocyanate (1.2 g, 7.9 mmol) in 1,2-dichloroethane (10 ml) was added dropwise over two minutes. This gave an initial solution followed by a thick precipitate. The mixture was heated at a gentle reflux for one hour, which gave a solution and then was allowed to cool to room temperature. The precipitate was collected, washed with dichloroethane and then hexanes, and dried in vacuo; 2.82 g, 89% yield. mp 133–40° C. [a$_D$] 49.6° (c=0.42, MeOH) $^1$H NMR (CDCl$_3$ with several drops dimethylsulfoxide DMSO-d$_6$) δ 8.83 (s, 1), 8.48 (s, 1), 7.30 (s, 1), 6.90–6.71 (m, 8), 6.61 (d, 1), 6.54–6.38 (m, 3), 4.20 (q, 1), 403 (q, 1), 2.70 (m, 1), 2.15 (m, 1), 1.96 (s, 3).

Under similar conditions as described above, the following cis-3-amino-5substituted-1,3,4,5tetrahydro-benzazepin-2-ones were reacted with 3chlorophenyl isocyanate to provide the corresponding ureas.

B. 3-[3-(3-Chlorophenyl)ureido]-5-cyclohexyl-2-oxo-1,3,4,5-tetrahydro-benzo[b]azepine Yield 1.17 g, 91%. mp 222–5° C. IR (KBr) 1694,1651 cm$^{-1}$. $^1$H NMR (DMSO -d$_6$) δ 9.88 (s, 1), 8.99 (s, 1), 7.60 (t, 1), 7.30–7.06 (m, 5), 6.98 (d, 1), 6.90 (d, 1), 6.60 (d, 1), 4.20 (m, 1), 2.58 (m, 2), 1.96 (m, 2), 1.76 –1.43 (m, 4), 1.22–0.77 (m, 5), 0.53 (m, 1). Mass spectrum: m/e 412 (M+1).

C. 3-[3-(3-Chlorophenyl)ureido]-5-cyclohexyl-8-methyl-2-oxo-1,3,4,5-tetrahydro-benzo[b]azepine Yield 0.193 g, 62%. mp 162–9° C. IR (KBr) 1674, 1619, 1592, 1554, 1515 cm$^{-1}$. $^1$H NMR (DMSO -d$_6$) δ 9.78 (s, 1), 8.96 (s, 1), 7.59 (s, 1), 7.20 (t, 1), 7.10 (d, 1), 7.04 (d, 1), 6.90 (d, 2), 6.76 (s, 1), 6.58 (d, 1), 4.19 (m, 1), 2.51 (m, 3), 2.27 (s, 3), 1.90 (m, 2), 1.71–1.43 (m, 4), 1.18–0.72 (m, 5), 0.48 (m, 1). Mass spectrum: m/e 426 (M+1).

D. 3-[3-(3-Chlorophenyl)ureido]-5-methyl-7,8-dimethoxy-2-oxo-1,3,4,5-tetrahydro-benzo[b]azepine:

Yield 0.33 g, 82%. mp 208–10° C. IR (KBr) 1725, 1707, 1696, 1676 cm$^{-1}$. $^1$H NMR (DMSO -d$_6$) δ 9.68 (s, 1), 9.00 (s, 1), 7.60 (t, 1), 7.20 (t, 1), 7.10 (dd, 1), 6.91 (dd, 1), 6.85 (s, 1), 6.61 (s,1), 6.55 (d, 1), 4.29 (m, 1), 3.28 (s, 3), 3.71 (s, 3), 3.04 (m, 1), 2.72 (m, 1), 1.63 (t, 1), 1.20 (d, 3). Analysis Calcd. for C$_{20}$H$_{22}$N$_3$O$_4$Cl: C, 59.47; H, 5.49; N, 10.40. Found: C, 59.28; H, 6.25; N, 9.76.

E. 6-[3-(3-Chlorophenyl)ureido]-7,7a-dihydro-4H,6H-fluoreno[1,9-bc]-azepine-5-one:

Yield 0.28 g, 67%. mp 221–225° C. IR (KBr) 1663, 1617, 1593, 1552 cm$^{-1}$. $^1$H NMR (DMSO-d$_6$) δ 10.29 (s, 1), 9.04 (s, 1), 7.90 (d, 1), 7.71 (d, 1), 7.56 (m, 2), 7.48 –7.33 (m, 3), 7.20 (t, 1), 7.09 (d, 1), 6.99 (d, 1), 6.90 (d, 1), 6.76 (d, 1), 4.30–4.14 (m, 2), 2.80 (q, 1), 2.30 (m, 1).

PREPARATION 10

N-tert-Butyl-2-{3(R)-[3-(3-chloro-phenyl)-ureido]methyl-2-oxo-5(R)-phenyl-2,3,4,5-tetrahydro-benzo[b]azepin-1-yl}-acetamide:

(+)-3(R)-[3-(3-Chloro-phenyl)-ureido]-8-methyl-2-oxo-5(R)-phenyl-1,3,4, 5-tetrahydro-benzo[b]azepine (2.5 g, 6 mmol), N-tert.-butyl iodoacetamide (1.72 g, 7.15 mmol) and tetrabutylammonium bromide (0.2 g, 0.6 mmol) were dissolved in dry tetrahydrofuran (50 ml) under a nitrogen atmosphere. Powder potassium hydroxide (0.45 g, 8 mmol) was added in one portion and the reaction was stirred at room temperature for 4 hours. The reaction was diluted with ethyl acetate (50 ml) and was washed with water and brine. After drying over magnesium sulfate, the solvent was removed in vacuo to provide a foam that was purified by flash chromatography over silica gel with 1:1 ethyl acetate: hexanes. The fractions with the product spot were combined and the material was crystallized from methanol and water to provide a white solid, 2.2 g, 71% yield. mp 156–170° C. [$\alpha_D$] 124.5° (c=0.52, $CH_2Cl_2$). $^1$H NMR ($CDCl_3$) δ 8.01 (s, 1), 7.60 (s, 1), 7.32 (d, 1), 7.24 (m, 2), 7.15 (m, 4), 7.02 (m, 2), 6.90 (d,1), 6.83 (d, 1), 6.75 (bs, 1), 5.88 (s, 1), 4.63 (t, 1), 4.29 (d, 1), 3.88 (d, 1), 3.02 (d, 2), 2.89 (d, 1), 2.39 (s, 3), 1.32 (s, 9).

PREPARATION 11

N-tert-Butyl-2-{3-[3-(3-chloro-phenyl)-ureido]-2-oxo-5-cyclohexyl-1,3,4,5-tetrahydro-benzo[b]azepin-1-yl}-acetamide:

Following the previous expermental procedure, 3-[3-(3-chloro-phenyl)-ureido]-2-oxo-5-cyclohexyl-1,3,4,5-tetrahydro-benzo[b]azepine (0.4 g, 1 mmol) was alkylated with N-tert.-butyl iodoacetamide (0.28 g, 1.2 mmol) to provide the title compound as a white solid, 0.3 g, 59% yield. mp 222–5° C. $^1$H NMR ($CDCl_3$) δ 8.03 (s, 1), 7.59 (t, 1), 7.34–7.15 (m, 3), 7.10 (d, 1),7.01 (t, 1), 6.91 (d, 1), 6.83 (d, 1), 6.43 (bd, 1), 6.43 (bd, 1), 6.31 (s, 1), 4.95 (d, 1), 4.54 (m, 1), 3.59 (d, 1), 2.66 (m, 1), 2.53 (t, 1), 2.18 (bd, 1), 1.78 (m, 1), 1.59 (m, 1), 1.4 (s, 9), 1.29–0.78 (m, 6), 0.58 (m, 1).

PREPARATION 12

3-[Tert.-butoxycarbonylamino]-8-methyl-2-oxo-5-phenyl-1,3,4,5-tetrahydro-benzo[b]azepine:

3Amino-8-methyl-2-oxo-5-phenyl-1,3,4,5-tetrahydro-benzo[b]azepine (1 g, 3.76 mmol) was suspended in methylene chloride (10 ml) under a nitrogen atmosphere. Triethylamine (0.38 g, 3.76 mmol) and di-t-butyl dicarbonate (0.82 g, 3.76 mmol) were added and the reaction was stirred at room temperature for 2 hours. The reaction was washed with 1 N HCl and brine, dried over magnesium sulfate, and evaporated in vacuo. The desired carbamate was isolated as a white foam which was used in the following reaction without further purification. $^1$H NMR ($CDCl_3$) δ 7.69 (s, 1), 7.24–7.06 (m, 6), 6.94 (d, 1), 6.73 (s, 1), 5.73 (d, 1), 4.49 (m, 1), 4.40 (m, 1), 2.99 (m, 1), 2.50 (m, 1), 2.30 (s, 3), 1.43 (s, 9).

PREPARATION 13

N-tert-Butyl-2-{3-[tert.-butoxycarbonylamino]-8-methyl-2-oxo-5-phenyl-1,3,4,5-tetrahydro-benzo[b]azepin-1-yl}-acetamide:

3-[Tert.-butoxycarbonylamino]-8-methyl-2-oxo-5-phenyl-1,3,4,5-tetrahydro-benzo[b]azepine (1.4 g, 3.8 mmol), N-t-butyl iodoacetamide (1.1 g, 4.56 mmol) and tetrabutylammonium bromide (85 mg, 0.26 mmol) were dissolved in dry tetrahydrofuran (25 ml) under nitrogen. Powder potassium hydroxide (0.3 g, 4.5 mmol) was added in one portion and the reaction was stirred for 5 hours. The reaction was diluted with ethyl acetate (25 ml) and washed with water (2×50 ml) and brine. After drying over magnesium sulfate, the solvent was evaporated in vacuo to provide the desired product as a foam; 2 g, >100% yield. This contained some excess iodoacetamide, but was suitable for use in the next reaction. IR (KBr) 1720, 1680, 1659, 1614 $cm^{-1}$. $^1$H NMR ($CDCl_3$) δ 7.28–7.07 (m, 6), 7.00 (d, 2), 6.05 (s, 1), 5.49 (d, 1), 4.34 (m, 1), 4.08 (d, 1), 3.62 (d, 1), 2.95 (dt, 1), 2.63 (t, 1), 2.60 (d, 1), 2.33 (s, 3), 1.41 (s, 9), 1.32 (s, 9).

PREPARATION 14

N-tert-Butyl-2-{3-amino-8-methyl-2-oxo-5-phenyl-1,3,4,5-tetrahydro-benzo[b]azepin-1-yl}-acetamide:

N-tertButyl-2-{3-[tert.-butoxycarbonylamino]-8-methyl-2-oxo-5-phenyl-1,3,4,5-tetrahydro-benzo[b]azepin-1-yl}-acetamide (1.2 g, 2.5 mmol) was dissolved in methylene chloride (10 ml) under a nitrogen atmosphere and cooled to 5° C. in an ice bath. Trifluoroacetic acid (10 ml) was added dropwise over 15 minutes and the reaction was stirred at ice bath temperature for four hours. The reaction was evaporated in vacuo and the residue was dissolved in ethyl acetate. The organic solution was extracted with 1N HCl (3×30 ml). The acidic aqueous layers were combined, ethyl acetate was added and the pH was adjusted to pH 10.5 by the addition of solid sodium carbonate. The organic layer was separated and the aqueous layer was extracted with ethyl acetate again. The combined ethyl acetate solutions were washed with brine, dried over magnesium sulfate, and evaporated in vacuo to provide the amine as a white foam, 0.62 g, 65% yield. $^1$H NMR ($CDCl_3$) δ 7.28–696 (m, 8), 6.00 (bs, 1), 4.14 (d, 1), 3.62–3.50 (m, 2), 2.79 (m, 1), 2.61 (m, 2), 2.35 (s, 3), 2.08 (bs, s), 1.30 (s, 9).

I claim:

1. The intermediate (+)-cis-(3R)-amino-8-methyl-(5R)-phenyl-1,3,4,5-tetrahydro-benzo[b]azepine-2-one.

2. A process for preparing the diastereomeric salt (+)cis-(3R)-amino-8-methyl-(5R)-phenyl-1,3,4,5-tetrahydro-benzo[b]azepine-2-one•(D)-(+)-dibenzoyltartarate or (−)-cis-(3S)-amino-8-methyl-(5S)-phenyl-1,3,4,5-tetrahydro-benzo[b]azepine-2-one•(L)-(−)-dibenzoyltartarate, comprising reacting (D)-(+)-dibenzoyltartaric acid with either racemic or optically enriched cis-3-amino-8-methyl-5-phenyl-1,3,4,5-tetrahydro-benzo[b]azepine-2-one, or reacting L-(−)-dibenzoyltartaric acid with either racemic or enantiomerically enriched cis-3-amino-8-methyl-5-phenyl-1,3,4,5-tetrahydro-benzo[b]azepine-2-one in an organic solvent.

3. A process according to claim 2, further comprising neutralizing the diastereomeric salt (+)-cis-(3R)-amino-8-methyl-(5R)-phenyl-1,3,4,5-tetrahydro-benzo[b]azepine-2-one•(D)-(+)-dibenzoyltartarate or (−)-cis-- (3S)-amino-8-methyl-(5S)-phenyl-1,3,4,5-tetrahydro-benzo[b]azepine-2-one•(L)-(+)-dibenzoyltartarate to form, respectively, (+)-cis-(3R)-amino-8-methyl-(5R)-phenyl-1,3,4,5tetrahydro-benzo[b]azepine-2-one or (−)-cis-(3S)-amino8-methyl-(5S)-phenyl-1,3,4,5-tetrahydro-benzo[b]azepin-2-one.

4. A process for preparing a compound of formula

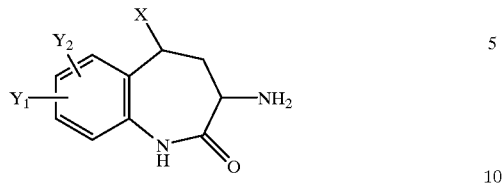

Ia wherein X and NH$_2$ are at least 90% in the cis configuration;

Y$^1$ and Y$^2$ are independently selected from halo, nitro, amino, (C$_1$–C$_6$)alkyl optionally substituted with from one to three fluorine atoms and (C$_1$–C$_6$)alkoxy optionally substituted with from one to three fluorine atoms, and X is selected from the group consisting of phenyl, (C$_3$–C$_8$)straight or branched alkyl and (C$_5$–C$_8$) cycloalkyl, wherein said phenyl may optionally be substituted with one or two substituents independently selected from the group consisting of halo, (C$_1$–C$_6$) alkyl, (C$_1$–C$_6$)alkoxy, nitro, amino and trifluoromethyl, and wherein said cycloalkyl may optionally be substituted with one or two substituents independently selected from (C$_1$–C$_6$)alkyl, comprising reducing a compound of the formula

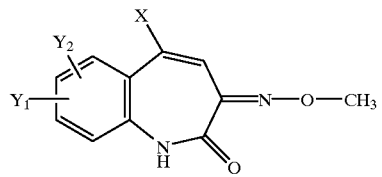

II wherein Y$^1$ and Y$^2$ are independently selected from halo, nitro, amino, (C$_1$–C$_6$)alkyl optionally substituted with from one to three fluorine atoms and (C$_1$–C$_6$) alkoxy optionally substituted with from one to three fluorine atoms, and X is selected from the group consisting of phenyl, (C$_3$–C$_8$)straight or branched alkyl and (C$_5$–C$_8$) cycloalkyl, wherein said phenyl may optionally be substituted with one or two substituents independently selected from the group consisting of halo, (C$_1$–C$_6$) alkyl, (C$_1$–C$_6$)alkoxy, nitro, amino and trifluoromethyl, and wherein said cycloalkyl may optionally be substituted with one or two substituents independently selected from (C$_1$–C$_6$)alkyl, with Raney-nickel and a hydrogen source.

* * * * *